(12) United States Patent
Watanabe et al.

(10) Patent No.: US 9,173,902 B2
(45) Date of Patent: Nov. 3, 2015

(54) SKIN-WHITENING AGENT

(75) Inventors: Tatsuya Watanabe, Fuchu (JP); Ken Kato, Kawagoe (JP); Hiroshi Ueno, Kawagoe (JP); Yuko Haruta, Kawagoe (JP); Noriko Ueda, Kawagoe (JP); Toshimitsu Yoshioka, Kawagoe (JP)

(73) Assignee: MEGMILK SNOW BRAND CO., LTD., Sapporo (JP)

( * ) Notice: Subject to any disclaimer, the term of this patent is extended or adjusted under 35 U.S.C. 154(b) by 612 days.

(21) Appl. No.: 12/530,617

(22) PCT Filed: Mar. 10, 2008

(86) PCT No.: PCT/JP2008/054313
§ 371 (c)(1),
(2), (4) Date: Feb. 3, 2010

(87) PCT Pub. No.: WO2008/111562
PCT Pub. Date: Sep. 18, 2008

(65) Prior Publication Data
US 2010/0135941 A1    Jun. 3, 2010

(30) Foreign Application Priority Data

Mar. 13, 2007  (JP) ................................. 2007-063053
Nov. 19, 2007  (JP) ................................. 2007-299516

(51) Int. Cl.
| | |
|---|---|
| *A61K 8/00* | (2006.01) |
| *A61K 35/20* | (2006.01) |
| *A23C 9/152* | (2006.01) |
| *A23K 1/16* | (2006.01) |
| *A23K 1/18* | (2006.01) |
| *A23L 1/305* | (2006.01) |
| *A23L 2/52* | (2006.01) |
| *A61K 8/64* | (2006.01) |
| *A61K 38/01* | (2006.01) |
| *A61Q 19/02* | (2006.01) |

(52) U.S. Cl.
CPC ............... *A61K 35/20* (2013.01); *A23C 9/1526* (2013.01); *A23K 1/1631* (2013.01); *A23K 1/1846* (2013.01); *A23L 1/3053* (2013.01); *A23L 2/52* (2013.01); *A61K 8/64* (2013.01); *A61K 38/018* (2013.01); *A61Q 19/02* (2013.01); *A61K 2800/92* (2013.01)

(58) Field of Classification Search
CPC ......... A61K 35/20; A61K 8/64; A61K 38/18; A61K 2800/92; A61Q 19/02; A23C 9/1526; A23K 1/1631; A23K 1/1846; A23L 1/3053; A23L 2/52

See application file for complete search history.

(56) References Cited

U.S. PATENT DOCUMENTS

| 5,219,838 A   * | 6/1993 | Tomita et al. ................. 514/18.6 |
| 2006/0171992 A1* | 8/2006 | Gerhardt et al. ............... 424/439 |
| 2007/0122454 A1 | 5/2007 | Yoshimura et al. |

FOREIGN PATENT DOCUMENTS

| JP | 02-002319 | 1/1990 | |
| JP | 02-138991 | 5/1990 | |
| JP | 04-069315 | 3/1992 | |
| JP | 04-112753 | 4/1992 | |
| JP | 04-112753 A * | 4/1992 | ............... A23J 3/34 |
| JP | 04-187619 | 7/1992 | |
| JP | 05-209000 | 8/1993 | |
| JP | 07-252126 | 10/1995 | |
| JP | 08-098656 | 4/1996 | |
| JP | 09-030928 | 2/1997 | |
| JP | 10-218755 | 8/1998 | |
| KR | 10-2006-0121240 | 11/2006 | |
| WO | WO 2005/063196 A1 | 7/2005 | |
| WO | WO 2008/088472 A2 | 7/2008 | |

OTHER PUBLICATIONS

Antonio Guadix et al.,"Production of whey protein hydrolysates with reduced allergenicity in a stable membrane reactor," J. of Food Engineering, 72 (2006) pp. 398-405.

The Extended European search report mailed by European Patent Office on Jun. 26, 2012 in the corresponding European patent application No. 08721726.5.

Notification of reason for refusal mailed by Korean Patent Office mailed Apr. 25, 2014 in the corresponding Korean Patent Application No. 10-2009-7019635—12 pages.

* cited by examiner

*Primary Examiner* — Johann R Richter
*Assistant Examiner* — David Browe
(74) *Attorney, Agent, or Firm* — Knobbe, Martens, Olson & Bear LLP

(57) ABSTRACT

A skin-whitening agent offering an excellent whitening effect and being effective in preventing and treating age spots, freckles, etc., where such skin-whitening agent contains as its effective ingredient a whey protein hydrolyzate characterized by a molecular weight distribution of 10 kDa or less, main peak of 200 Da to 3 kDa, APL (average peptide-chain length) of 2 to 8, free amino acid content of 20% or less, and antigenicity of one-ten thousandth of β-lactoglobulin or less, as well as a cosmetic, drink or food, feed, pharmaceutical preparation or other skin-whitening product containing such skin-whitening agent.

2 Claims, No Drawings

SKIN-WHITENING AGENT

This application is the U.S. National Phase under 35 U.S.C. §371 of International Application PCT/JP2008/054313, filed Mar. 10, 2008, which claims priority to Japanese Patent Application No. 2007-063053, filed Mar. 13, 2007, and No. 2007-299516, filed Nov. 19, 2007. The International Application was published under PCT Article 21(2) in a language other than English.

TECHNICAL FIELD

The present invention relates to a skin-whitening agent offering an excellent skin whitening effect, being effective in preventing and treating age spots, freckles, etc., having little bitterness, and demonstrating excellent stability and safety.

The present invention also relates to a skin-whitening cosmetic, skin-whitening drink or food, skin-whitening nutritional composition, skin-whitening feed or skin-whitening pharmaceutical preparation that contains such skin-whitening agent.

PRIOR ART

The color of skin is determined mainly by the types and quantities of melanin, hemoglobin, carotinoid and other coloring components in the epidermis and dermis. The types and quantities of these coloring components in the epidermis and dermis are not constant, but they are controlled by various external and internal factors. Melanin pigment is synthesized in the skin mainly by melanocytes, and activated by stimulation by ultraviolet light, secretion of hormones and stimulants released by the surrounding keratinocytes. One key role of melanin pigment is to reduce skin problems caused by ultraviolet light. However, excessive synthesis of melanin pigment or abnormal metabolism of melanin pigment can cause local pigmentation, which manifests in the forms of so-called age spots, freckles and other unsightly conditions, causing significant cosmetic problems.

Methods to improve pigmentation of skin include suppression of melanin production within melanocytes, reduction of existing melanin, promotion of release of melanin from the epidermis, and selective poisoning of melanocytes. Among others, L-ascorbic acid having a reducing action and its derivatives are widely used as skin-whitening substances. However, they do not produce a sufficient skin-whitening effect.

In addition, hydroquinone, arbutin, kojic acid, licorice extract, placenta extract and other inhibitors of tyrosinase, which is a melanin synthesizing enzyme, are also used as skin-whitening agents. However, these substances present problems in terms of stability, safety, etc., and therefore the market has been waiting for development of new skin-whitening agents.

It should also be noted that, although the tyrosinase activity inhibiting action exhibited by hydrolyzates of lactic protein has been reported in Patent Literature 1, the invention described therein is limited regarding its actual use in products because an aqueous solution of the applicable decomposition product is whitely cloudy, or specifically the aforementioned invention has a drawback in that it cannot be used in products that require transparency. Also, the aforementioned invention presents a unique bitterness of peptide, and this bitterness limits the flavors that can be achieved when the aforementioned invention is used in the manufacture of food, feed, pharmaceutical preparation and other products that are eaten or taken orally.

On the other hand, hydrolyzates of lactic protein are used in various products for the purpose of preventing food allergies triggered by cow milk and milk products. In particular, whey protein contained in cow milk is believed to serve as an allergen, unlike protein contained in mother's milk. One known method to prevent whey protein from becoming an allergen is to hydrolyze whey protein using an enzyme. Manufacturing methods reflecting this concept are reported in Patent Literature 2 and Patent Literature 3, among others.

However, use of these methods or specifically the methods of manufacturing a whey protein hydrolyzate presents many problems like the ones listed below, because the methods involves heating and deactivation of the enzyme after the enzyme treatment, as well as subsequent additional enzyme treatment: 1) The precipitate and aggregate of whey protein that generate after heating and enzyme deactivation are difficult to treat using an enzyme, which suppresses a drop in the antigenicity and prevents the yield from improving; and 2) if the whey protein is heated (at 90° C. for 10 minutes or more) beforehand prior to the enzyme treatment, the yield drops.

To solve the aforementioned problems, the inventors of the present invention had earlier developed and patented a method of manufacturing a whey protein hydrolyzate that can be obtained by adding a heat-resistant protein hydrolyzing enzyme to a whey protein under certain conditions and then thermally denaturing the whey protein to break it down using the enzyme (Patent Literature 4). However, although the whey protein hydrolyzate obtained by this manufacturing method was confirmed to demonstrate low allergen property in itself, the inventors never thought about its function as a skin-whitening agent. The inventors also found that filtering the hydrolyzate through ultrafiltration (UF) membranes or microfiltration (MF) membranes would improve the skin-whitening effect even further.

Patent Literature 1: Japanese Patent Laid-open No. Hei 4-69315
Patent Literature 2: Japanese Patent Laid-open No. Hei 2-2319
Patent Literature 3: Japanese Patent Laid-open No. Hei 2-138991
Patent Literature 4: Japanese Patent Laid-open No. Hei 4-112753

SUMMARY OF THE INVENTION

Problems to be Solved by the Invention

In view of the above, it is one object of the present invention to provide a skin-whitening agent constituted by a whey protein hydrolyzate offering excellent safety, presenting high transparency in an aqueous solution state, having little bitterness and therefore not limiting flavors, presenting no limitations regarding its use in products, and having a skin-whitening effect.

In addition, it is another object of the present invention to provide a skin-whitening cosmetic offering excellent safety or skin-whitening drink or food, skin-whitening nutritional composition, skin-whitening feed or skin-whitening pharmaceutical preparation eaten or taken orally which exhibits excellent safety and presents no flavoring problems, all of which having a skin-whitening function.

Means for Solving the Problems

To achieve the aforementioned objects, the inventors of the present invention examined in earnest the physical properties of a whey protein hydrolyzate that can be obtained, as mentioned above, by adding a heat-resistant protein hydrolyzing enzyme to a whey protein under certain conditions and then thermally denaturing the whey protein to break it down using the enzyme, and the inventors consequently found that a whey protein hydrolyzate whose molecular weight distribution is 10 kDa or less, main peak is 200 Da to 3 kDa, APL (average peptide-chain length) is 2 to 8, free amino acid content to all constituents is 20% or less, and antigenicity is one-ten thousandth of that of β-lactoglobulin or less, would provide a skin-whitening effect meeting the aforementioned objects.

In summary, the present invention encompasses the following constitutions:

(1) A skin-whitening agent characterized by comprising, as an effective ingredient, a whey protein hydrolyzate having the following characteristics:
  (A) the molecular weight distributed within 10 kDa with a main peak of 200 Da to 3 kDa;
  (B) the APL (average peptide-chain length) is 2 to 8;
  (C) the free amino acid content is 20% or less; and
  (D) the antigenicity is one-ten thousandth of antigenicity of β-lactoglobulin or less.

(2) The skin-whitening agent according to (1), characterized in that the whey protein hydrolyzate contained as the effective ingredient is obtained by enzymatically decomposing a whey protein while thermally denaturing the whey protein using a heat-resistant protein hydrolyzing enzyme under pH 6 to 10 at 50 to 70° C., and then heating the obtained product and thereby deactivating the enzyme.

(3) A skin-whitening agent according to (1), characterized in that the whey protein hydrolyzate contained as the effective ingredient is obtained by enzymatically decomposing a whey protein using a protein hydrolyzing enzyme under pH 6 to 10 at 20 to 55° C., and then heating the obtained product to 50 to 70° C., and then enzymatically decomposing not-yet-broken down whey protein by using a heat-resistant protein hydrolyzing enzyme while thermally denaturing the not-yet-broken down whey protein under pH 6 to 10 at 50 to 70° C., and then heating the obtained product and thereby deactivating the enzyme.

(4) A skin-whitening cosmetic, skin-whitening drink or food, skin-whitening nutritional composition, skin-whitening feed or skin-whitening pharmaceutical preparation, characterized by comprising a skin-whitening agent according to any one of (1) to (3) above.

Effects of the Invention

A skin-whitening agent conforming to the present invention exhibits prominent tyrosinase activity inhibition action, melanin production inhibition effect, and pigmentation prevention/improvement effect, and this skin-whitening agent offers an excellent skin-whitening effect and is effective in preventing and treating age spots, freckles and the like.

As explained later, the whey protein hydrolyzate used in this skin-whitening agent as an effective ingredient has been confirmed to have an antigenicity of one-ten thousandth or less relative to β-lactoglobulin, and one-ten thousandth of whey protein or less, and is therefore extremely safe.

Also, an aqueous solution of the skin-whitening agent is transparent and has a bitterness of approx. 2, thereby presenting no limitations when the aqueous solution is used as a skin-whitening agent. In particular, it can be blended at a high ratio in any skin-whitening agent that requires transparency.

In addition, the present invention can provide a skin-whitening cosmetic offering excellent safety, or skin-whitening drink or food, skin-whitening nutritional composition, skin-whitening feed or skin-whitening pharmaceutical preparation eaten or taken orally which exhibits excellent safety and presents no flavoring problems, where such product contains the aforementioned skin-whitening agent as an effective ingredient and has a skin-whitening function.

Furthermore, a skin-whitening agent conforming to the present invention uses whey protein as its material and thus can be produced easily in a simple and economical way.

BEST MODE FOR CARRYING OUT THE INVENTION

The whey protein hydrolyzate contained in a skin-whitening agent conforming to the present invention is a whey protein hydrolyzate having a skin-whitening action, obtained by enzymatically decomposing a whey protein while thermally denaturing the whey protein using a heat-resistant protein hydrolyzing enzyme under pH 6 to 10 at 50 to 70° C., and then heating the obtained product and thereby deactivating the enzyme. The yield can be enhanced further if the whey protein of pH 6 to 10 is broken down using a protein hydrolyzing enzyme at temperatures of 20 to 55° C. prior to the aforementioned enzyme breakdown process, and then immediately implementing another enzyme breakdown process under the aforementioned conditions without cooling it down first.

Take note that the skin-whitening effect can be enhanced further if the whey protein hydrolyzate prepared as above is concentrated by a method selected from the group that contains use of ultrafiltration (UF) membranes with a molecular weight cut off in a range of 1 kDa to 20 kDa or preferably 2 kDa to 10 kDa and/or microfiltration (FM) membranes with a molecular weight cut off in a range of 100 Da to 500 Da or preferably 150 Da to 300 Da. It is also possible to reduce the bitterness and improve the transparency further.

The whey protein used in the present invention may be a whey from cow, buffalo goat, human or any other mammal, or aggregate, powder or refined protein made therefrom, and when this whey protein is reacted with an enzyme it is used in an aqueous solution state.

When adjusting this solution to pH 6 to 10, normally no special pH adjustment is required because generally whey proteins have pH in this range. If pH adjustment is necessary, however, an acid solution containing hydrochloric acid, citric acid, lactic acid, etc., or alkali solution containing caustic soda, calcium hydroxide, sodium phosphate, etc., is used to adjust the pH to a range of 6 to 10. Although heating is performed at temperatures of 50 to 70° C., if a heat-resistant protein hydrolyzing enzyme is used it is better to add the enzyme before the heating to initiate enzyme breakdown, rather than adding it after adjusting the temperature to the aforementioned range, from the viewpoint of yield.

An optimal temperature is 40° C. or below in the case of a general protease. With a heat-resistant protein hydrolyzing enzyme, however, an optimal temperature is 45° C. or above. Any heat-resistant protein hydrolyzing enzyme can be used without any limitation, as long as it has been known as a heat-resistant protein hydrolyzing enzyme having such optimal temperature. Examples of such heat-resistant protein hydrolyzing enzyme include papain, Protease S (product name), Proleather (product name), Thermoase (product name), Alcalase (product name), and Protin A (product name), among others. It is desirable that the heat-resistant protein hydrolyzing enzyme will have a remaining activity of approx. 10% or more after heating at 80° C. for 30 minutes. It is also more effective to use multiple enzymes than using only one enzyme. The reaction time is preferably 30 minutes to 10 hours or so.

Lastly, the reaction solution is heated to deactivate the enzyme. The enzyme can be deactivated by heating the reaction solution at 100° C. or above for 10 seconds or more.

Next, the reaction solution is centrifugally separated and the supernatant is collected, which is then dried to make a power product. In the above, the degree of the precipitate that generates during the centrifugal separation process becoming a low allergen is lower than the supernatant and thus preferably it should be removed. However, it goes without saying that the reaction solution can also be dried and used directly.

The whey protein hydrolyzate obtained by this method has been measured based on the Inhibition ELISA method (Journal of Japanese Society of Pediatric Allergy and Clinical Immunology, 1, 36 (1987)) and confirmed to have an antigenicity of one-ten thousandth of β-lactoglobulin or less, or one-ten thousandth of whey protein, which indicates that this whey protein hydrolyzate is extremely safe. In addition, an aqueous solution of the whey protein hydrolyzate is transparent and its bitterness is approx. 2, thereby presenting no limitations on use in products. Take note that the transparency and bitterness were evaluated using the methods specified below.

Transparency evaluation method: A 1% whey protein hydrolyzate solution was prepared and its absorbency was measured at 650 nm.

Bitterness evaluation method: A 10% whey protein hydrolyzate solution was prepared and a quinine hydrochloride, which is a bitter substance, was added to evaluate the bitterness. As shown in Table 1, a substance can be used in drinks, food, etc., if its bitterness score is 2 points or less.

TABLE 1

| Quinine hydrochloride concentration | Bitterness score |
| --- | --- |
| 0.004% | 1 (Weak) |
| 0.010% | 2 |
| 0.020% | 3 (Strong) |

Although a whey protein hydrolyzate conforming to the present invention can be used directly as a skin-whitening agent, it can also be made into powder, granule, tablet, capsule, drink or other dosage forms according to normal methods and used as such. In addition, a whey protein hydrolyzate obtained by filtering through ultrafiltration (UF) membranes and microfiltration (MF) membranes can be used directly as a skin-whitening agent, or it can be dried and used. Of course, it can be made into various formulations according to normal methods.

It is also possible to blend these various dosage forms in nutritional supplements, yogurt, milk drinks, wafers and other drink and food products, nutritional compositions, feeds and pharmaceutical preparations.

A skin-whitening drink or food, skin-whitening nutritional composition, skin-whitening feed or skin-whitening pharmaceutical preparation conforming to the present invention may contain only the aforementioned whey protein hydrolyzate, but it can also contain in addition to the whey protein hydrolyzate any stabilizer, sugar, lipid, flavoring agent, vitamin, mineral, flavonoid, polyphenol or other material or agent normally contained in drinks and food, feeds and pharmaceutical preparation.

It is also possible to use such skin-whitening drink or food, skin-whitening nutritional composition, skin-whitening feed or skin-whitening pharmaceutical preparation as a material and then add other material or agent normally contained in drinks and food, etc., to prepare a final product.

The blending amount of a whey protein hydrolyzate in a skin-whitening drink or food, skin-whitening nutritional composition, skin-whitening feed or skin-whitening pharmaceutical preparation is not specifically limited, but to make sure an adult orally ingests at least 5 mg of whey protein hydrolyzate per day, this blending amount is adjusted preferably to a range of 0.001 to 10% (weight/weight), or more preferably to a range of 0.1 to 5% (weight/weight), relative to the total mass, although the specific amount varies depending on the form of the drink, food, feed or pharmaceutical preparation.

In the case of a skin-whitening cosmetic, the present invention can be used in a cosmetic of any normal form such as milk, cream, lotion or mask. These cosmetics can be manufactured using any normal method, where a whey protein hydrolyzate can be added in the manufacturing process as deemed appropriate. It is also possible to use any such cosmetic as a material to manufacture another cosmetic. The blending amount of a whey protein hydrolyzate in a cosmetic is not specifically limited, but the blending amount is adjusted preferably to a range of 0.001 to 30% (weight/weight), or more preferably to a range of 0.1 to 10% (weight/weight), relative to the total mass.

A skin-whitening agent conforming to the present invention can be prepared into a desired dosage form by adding appropriate auxiliaries to the aforementioned effective ingredient, to obtain a skin-whitening composition that can be taken orally or administered parenterally. When preparing a dosage form, any normal filler, extender, binder, disintegrator, surface active agent, lubricant or any other type of diluent or excipient can be used.

If the present invention is used as a pharmaceutical preparation, any one of various forms can be selected. Examples include capsule, tablet, granule, dispersant, liquid, suspension, emulsion, suppository, injection, and ointment, among others. Examples of excipients include sucrose, milk sugar, starch, crystalline cellulose, mannite, light silicic anhydride, magnesium aluminate, synthetic aluminum silicate, metasilicate magnesium aluminate, calcium carbonate, sodium hydrogen carbonate, calcium hydrogen phosphate, carboxyl methyl cellulose calcium, etc., where only one of the foregoing types of excipients may be added or two or more types may be combined and added.

EXAMPLES

Examples, comparative examples and test examples are shown below to explain the present invention in detail. It should be noted, however, that these are only examples and the present invention is not at all limited to these examples.

Example 1

One liter of 10% aqueous solution of whey protein was mixed with 50 U of papain per 1 g of whey protein and 150 U of Proleather (by Amano Enzyme Inc.) per 1 g of whey protein, after which the pH was adjusted to 8 and then the whey protein was denatured at 55° C. for 6 hours to implement enzyme breakdown. Next, the reaction solution was heated at 100° C. for 15 seconds or more to deactivate the enzyme, and then the resulting solution was centrifugally separated and the supernatant was collected and dried to obtain a whey protein hydrolyzate (HW).

The molecular weight distribution of the obtained whey protein hydrolyzate (HW) was 10 kDa or less, while its main peak was 1.3 kDa, APL was 7.2, and free amino acid content to all constituents was 18.9%.

When the drop in the antigenicity to β-lactoglobulin was measured using the Inhibition ELISA method, the final antigenicity was one-ten thousandth or less, while the yield (percentage (%) by dry weight of the supernatant relative to the input amount by dry weight after the enzyme reaction solution was centrifugally separated) was 80.3% and the bitterness was 2.

The whey protein hydrolyzate thus obtained can be utilized directly as a skin-whitening agent conforming to the present invention.

Example 2

One liter of 10% aqueous solution of whey protein was mixed with 50 U of papain per 1 g of whey protein and 150 U of Proleather (by Amano Enzyme Inc.) per 1 g of whey protein, after which the pH was adjusted to 8 and enzyme breakdown was performed at 50° C. for 3 hours. The obtained solution was heated to 55° C. and kept at that temperature for 3 hours to denature the protein and break down the protein using the enzyme, after which the solution was heated at 100° C. for 15 seconds or more to deactivate the enzyme. The reaction solution was filtered through UF membranes with a molecular weight cut off of 10 kDa (by STC) and MF membranes with a molecular weight cut off of 300 Da (by STC), after which the concentrate fraction was collected and dried to obtain a whey protein hydrolyzate (HW).

The molecular weight distribution of the obtained whey protein hydrolyzate (HW) was 10 kDa or less, while its main peak was 500 Da, APL was 3.0, and free amino acid content to all constituents was 15.2%.

When the drop in the antigenicity to β-lactoglobulin was measured using the Inhibition ELISA method, the final antigenicity was one-ten thousandth or less, while the yield was 65.4% and the bitterness was 2.

The whey protein hydrolyzate thus obtained can be utilized directly as a skin-whitening agent conforming to the present invention.

In addition, the following lactoprotein hydrolyzates were prepared as described in Japanese Patent Laid-open No. Hei 4-69315 and used as comparative samples.

Comparative Example 1

120 g of whey protein was dissolved in 1,800 ml of purified water and then 1M caustic soda solution was added to adjust the pH to 7.0. Next, the solution was heated at 60° C. for 10 minutes to kill bacteria, after which the solution was kept at 45° C. and then 20 g of Amano A (by Amano Enzyme Inc.) was added to cause reaction for 2 hours. The resulting solution was heated at 80° C. for 10 minutes to deactivate the enzyme, after which the solution was freeze-dried to obtain a whey protein hydrolyzate.

The breakdown ratio of the obtained whey protein hydrolyzate was 18%, while its yield was 80.6%.

Comparative Example 2

120 g of whey protein was dissolved in 1,800 ml of purified water and then 1M caustic soda solution was added to adjust the pH to 7.0. Next, the solution was heated at 60° C. for 10 minutes to kill bacteria, after which the solution was kept at 45° C. and then 20 g of Amano A (by Amano Enzyme Inc.) was added to cause reaction for 8 hours. The resulting solution was heated at 80° C. for 10 minutes to deactivate the enzyme, after which the solution was freeze-dried to obtain a whey protein hydrolyzate.

The breakdown ratio of the obtained whey protein hydrolyzate was 30%, while its yield was 80.6%.

Comparative Example 3

200 g of casein was suspended in 2,000 ml of purified water and then 1M caustic soda solution was added to adjust the pH to 8.0, after which the mixture was dissolved completely. Next, the solution was heated at 80° C. for 10 minutes to kill bacteria, after which the solution was kept at 50° C. and then 20 g of Pancreatin F (by Amano Enzyme Inc.) and 20 g of Amano A (by Amano Enzyme Inc.) were added to cause reaction for 10 hours. The resulting solution was heated at 80° C. for 10 minutes to deactivate the enzymes, after which the solution was freeze-dried to obtain a casein hydrolyzate.

The breakdown ratio of the obtained casein hydrolyzate was 38%, while its yield was 77.8%.

Comparative Example 4

200 g of casein was suspended in 2,000 ml of purified water and then 1M caustic soda solution was added to adjust the pH to 8.0, after which the mixture was dissolved completely. Next, the solution was heated at 80° C. for 10 minutes to kill bacteria, after which the solution was kept at 40° C. and then 15 g of Pancreatin F (by Amano Enzyme Inc.) was added to cause reaction for 5 hours. The resulting solution was heated at 80° C. for 10 minutes to deactivate the enzyme, after which the solution was freeze-dried to obtain a casein hydrolyzate.

The breakdown ratio of the obtained casein hydrolyzate was 20%, while its yield was 79.1%.

Test Example 1

Transparency Test

A 1% aqueous solution of each of the protein hydrolyzates obtained in Examples 1 and 2 and Comparative Examples 1 to 4 was prepared and its absorbency was measured at 650 nm. The results are shown in Table 2.

TABLE 2

| Sample | Absorbency (650 nm) |
| --- | --- |
| HW (Example 1) | 0.008 |
| HW (Example 2) | 0.004 |
| (Comparative sample) | |
| Comparative Example 1 | 0.064 |
| Comparative Example 2 | 0.018 |
| Comparative Example 3 | 0.014 |
| Comparative Example 4 | 0.030 |

As shown by their low absorbencies, the whey protein hydrolyzates (HWs) obtained in Examples 1 and 2 had higher transparency. On the other hand, the comparative samples were found to be higher in absorbency and lower in transparency compared to the whey protein hydrolyzates obtained in Examples 1 and 2. In addition, the membrane-filtered whey protein hydrolyzate (HW) obtained in Example 2 had a lower absorbency and better transparency compared to the whey protein hydrolyzate (HW) obtained in Example 1.

Test Example 2

Tyrosinase Activity Inhibition Action

Tyrosinase is an enzyme that synthesizes melanin from tyrosine, where tyrosine is converted into dopa and then dopa into dopa quinone in the synthesis pathway. Tyrosinase (mushroom-derived type by Sigma-Aldrich, Inc.) was used to pre-treat the whey protein hydrolyzate (HWs) obtained in Examples 1 and 2 and comparative samples (Comparative Examples 1 to 4) at 37° C. for 15 minutes. Dopa (by Sigma-Aldrich, Inc.) was added as the matrix and to cause reaction further at 37° C. for 5 minutes, after which the absorbency at 476 nm was measured. The inhibition ratio was calculated based on 100% representing the value when nothing was added.

The results are shown in Table 3.

TABLE 3

| Sample | Concentration (% by mass) | Inhibition ratio (%) |
|---|---|---|
| HW (Example 1) | 0.01 | 16.1 |
|  | 0.1 | 26.7 |
|  | 1.0 | 40.8 |
| HW (Example 2) | 0.01 | 17.5 |
|  | 0.1 | 28.8 |
|  | 1.0 | 44.0 |
| (Comparative sample) |  |  |
| Comparative Example 1 | 0.01 | 10.2 |
|  | 0.1 | 19.5 |
|  | 1.0 | 22.6 |
| Comparative Example 2 | 0.01 | 15.4 |
|  | 0.1 | 19.2 |
|  | 1.0 | 28.1 |
| Comparative Example 3 | 0.01 | 9.2 |
|  | 0.1 | 12.4 |
|  | 1.0 | 13.6 |
| Comparative Example 4 | 0.01 | 13.6 |
|  | 0.1 | 19.2 |
|  | 1.0 | 23.6 |

As shown by the results in Table 3, the whey protein hydrolyzates (HW) obtained in Examples 1 and 2 suppressed enzyme activity in a manner dependent upon concentration within a concentration range of 0.01% to 1.0%. Some suppression effect was also observed with the comparative samples.

However, the whey protein hydrolyzates (HWs) obtained in Examples 1 and 2 showed a notably higher suppression effect compared to the comparative samples. It was also found that membrane filtration would improve the suppression effect further.

Test Example 3

Melanin Production Inhibition Test

Mouse malignant melanoma B16-F0 cells (purchased from Dainippon Sumitomo Pharma Co., Ltd.) were used. The cells were cultured in a $CO_2$ incubator (5% $CO_2$, 37° C.) using Eagle's MEM culture medium containing 10% fetal bovine serum (by Sigma-Aldrich, Inc.). A suspension with a B16 cell concentration of $3\times10^5$ cells/ml was prepared and 1 ml of this suspension was dispensed into a 100-mm dish containing 9 ml of culture medium. Next day, each culture medium was replaced with one containing each of the whey protein hydrolyzate (HWs) obtained in Examples 1 and 2 and comparative samples (Comparative Examples 1 to 4) by 0.01 to 1%, and the cells were cultured for 4 days. After the culturing, the cells were removed and the number of cells in each group was adjusted to $5\times10^6$, after which the cells were centrifuged.

The centrifuged cells were dissolved by adding 500 ml of 1 mol/L NaOH, and then the absorbency of the solution was measured at 405 nm.

Table 4 shows the calculated melanin production inhibition ratio of each group based on 100% representing the value of the group where nothing was added.

TABLE 4

Melanin production inhibition ratio of each group

| Sample | Concentration (% by mass) | Inhibition ratio (%) |
|---|---|---|
| HW (Example 1) | 0.01 | 19.4 |
|  | 0.1 | 29.8 |
|  | 1.0 | 48.4 |
| HW (Example 2) | 0.01 | 28.2 |
|  | 0.1 | 46.9 |
|  | 1.0 | 64.2 |
| (Comparative sample) |  |  |
| Comparative Example 1 | 0.01 | 14.3 |
|  | 0.1 | 22.4 |
|  | 1.0 | 30.0 |
| Comparative Example 2 | 0.01 | 19.0 |
|  | 0.1 | 26.2 |
|  | 1.0 | 35.2 |
| Comparative Example 3 | 0.01 | 10.8 |
|  | 0.1 | 11.3 |
|  | 1.0 | 15.7 |
| Comparative Example 4 | 0.01 | 12.2 |
|  | 0.1 | 18.5 |
|  | 1.0 | 22.6 |

As shown by Table 4, the whey protein hydrolyzates (HWs) obtained in Examples 1 and 2 had a concentration-dependent melanin production inhibition effect in a concentration range of 0.01% to 1.0%.

Although the comparative samples also exhibited some inhibition effect in a similar manner, the whey protein hydrolyzate (HW) conforming to the present invention had a better inhibition effect than the comparative samples. It was also found that membrane filtration would improve the inhibition effect further.

Test Example 4

Animal Test

Female A-1 guinea pigs weighing approx. 400 g and shaved at the back were irradiated on their back once a day for four days with ultraviolet light (30.3 $kJ/m^2$ of UVA (max. 360 nm) and 4.8 $kJ/m^2$ of UVB (max. 312 nm)). Next, the guinea pigs were separated into four test groups (each consisting of 10 guinea pigs) including a group administered with 5 ml of saline solution per 1 kg of guinea pig weight (group A), group administered with 2 mg/5 ml of the whey protein hydrolyzate (HW) obtained in Example 2 per 1 kg of guinea pig weight (group B), group administered with 5 mg/5 ml of HW per 1 kg of guinea pig weight (group C), and group administered with 10 mg/5 ml of HW per 1 kg of guinea pig weight (group D), and the guinea pigs in each group were raised for 4 weeks by orally administering each sample once a day using a sonde. How pigmentation of the back skin of the guinea pig was affected was measured at the start and end of sample administration using a colorimeter (CHROMA METER CR-200) by Minolta Co., Ltd. The recovery ratio was calculated from the difference between the luminosity before the irradiation of ultraviolet light and luminosity after the irradiation, based on 100% representing the luminosity before the irradiation.

The results are shown in Table 5.

TABLE 5

Melanin production inhibition ratio of each group

| Group | Administered amount of HW (mg/kg) | Luminosity recovery ratio (%) |
|---|---|---|
| Group A | 0 | 20.0 |
| Group B | 2 | 39.7 |
| Group C | 5 | 51.9 |
| Group D | 10 | 70.5 |

As shown from Table 5, groups B to D showed a notable improvement in luminosity. These results indicate that the whey protein hydrolyzate (HW) conforming to the present invention has a pigmentation prevention/improvement effect.

Test Example 5

Animal Test

Female A-1 guinea pigs weighing approx. 400 g and shaved at the back were irradiated on their back once a day for four days with ultraviolet light (30.3 kJ/m$^2$ of UVA (max. 360 nm) and 4.8 kJ/m$^2$ of UVB (max. 312 nm)). Next, the sample was applied continuously over the test area twice a day for four weeks. The test sample was dissolved in a mixture of water, ethanol and propylene glycol where the ingredients were mixed at a ratio of 2:2:1, and the obtained solution was applied.

The guinea pigs were separated into four test groups (consisting of 10 guinea pigs each) including a control group (group A) and groups where the whey protein hydrolyzate (HW) obtained in Example 2 was applied by 0.01% (group B), 0.1% (group C) and 1% (group D), respectively. How pigmentation of the back skin of the guinea pig was affected was measured at the start and end of sample application using a colorimeter (CHROMA METER CR-200) by Minolta Co., Ltd. The recovery ratio was calculated from the difference between the luminosity before the irradiation of ultraviolet light and luminosity after the irradiation, based on 100% representing the luminosity before the irradiation. The results are shown in Table 6.

TABLE 6

| Group | HW concentration (%) | Luminosity recovery ratio (%) |
|---|---|---|
| Group A | 0 | 17.2 |
| Group B | 0.01 | 36.7 |
| Group C | 0.1 | 67.0 |
| Group D | 1 | 77.5 |

As shown by the results in Table 6 above, groups B to D showed a notable improvement in luminosity. These results indicate that the whey protein hydrolyzate (HW) conforming to the present invention can also prevent/improve pigmentation through external application.

A skin-whitening agent obtained under the present invention, which contains as its effective ingredient a whey protein hydrolyzate whose composition is characterized by the (A) molecular weight distribution of 10 kDa or less and main peak of 200 Da to 3 kDa, (B) APL (average peptide-chain length) of 2 to 8, (C) free amino acid content of 20% or less, and (4) antigenicity of one-ten thousandth of β-lactoglobulin or less, has been confirmed to have an antigenicity of one-ten thousandth of β-lactoglobulin based on measurement according to the Inhibition ELISA method (Journal of Japanese Society of Pediatric Allergy and Clinical Immunology, 1, 36 (1987)), and therefore it is extremely safe.

In addition, an aqueous solution of this whey protein hydrolyzate is transparent and its bitterness is approx. 2, and therefore it is not subject to any limitations when used in products. This whey protein hydrolyzate has notable tyrosinase activity inhibition action, melanin production inhibition effect and pigmentation prevention/improvement effect.

Example 3

Preparation of Skin-Whitening Cosmetic (Cream)

The materials were mixed according to the blend shown in Table 7 to prepare a skin-whitening cosmetic (cream) conforming to the present invention.

TABLE 7

| Glycerin monostearate (self-emulsifying type) | 10.0 |
|---|---|
| Refined lanoline | 6.0 |
| Liquid paraffin | 5.0 |
| Jojoba oil | 5.0 |
| Paraben | 0.3 |
| HW obtained in Example 1 | 0.3 |
| Fragrance | As appropriate |
| Sterilized ion exchange water | As needed to make the total quantity 100.0 |

Example 4

Preparation of Skin-Whitening Cosmetic (Lotion)

The materials were mixed according to the blend shown in Table 8 to prepare a skin-whitening cosmetic (lotion) conforming to the present invention.

TABLE 8

| Sorbitol | 3.0 |
|---|---|
| DL-pyrrolidone sodium carboxylate | 2.0 |
| Carboxy methyl cellulose | 0.3 |
| Paraben | 0.1 |
| HW obtained in Example 2 | 0.1 |
| Fragrance | As appropriate |
| Sterilized ion exchange water | As needed to make the total quantity 100.0 |

Example 5

Preparation of Skin-Whitening Tablets

The materials were mixed according to the blend shown in Table 9, after which the mixture was formed and compressed into pieces weighing 1 g each, to produce skin-whitening tablets conforming to the present invention.

TABLE 9

| Hydrous crystalline glucose | 83.5 (% by weight) |
|---|---|
| HW obtained in Example 1 | 10.0 |
| Mineral mixture | 5.0 |
| Sugar ester | 1.0 |
| Fragrance | 0.5 |

In the above, 1 g of this tablet contained 100 mg of HW.

Example 6

Preparation of Skin-Whitening Liquid Nutritional Composition 50 g of HW obtained in Example 2 was dissolved in 4,950 g of deionized water, after which the solution was heated to 50° C. and then agitated and mixed for 30 minutes using a TK homogenizing mixer (TK ROBO MICS by Tokushu Kika Kogyo Co., Ltd.) operated at 6,000 rpm, to obtain a HW solution containing 50 g/5 kg of HW. Then, 5.0 kg of this HW solution was mixed with 5.0 kg of casein, 5.0 kg of soybean protein, 1.0 kg of fish oil, 3.0 kg of perilla oil, 18.0 kg of dextrin, 6.0 kg of mineral mixture, 1.95 kg of vitamin mixture, 2.0 kg of emulsifier, 4.0 kg of stabilizer, and 0.05 kg of fragrance, after which the mixture was filled in a 200-ml retort pouch and sterilized at 121° C. for 20 minutes using a retort sterilization machine (Class 1 pressure vessel, type RCS-4CRTGN by Hisaka Works, Ltd.), to produce 50 kg of a skin-whitening liquid nutritional composition conforming to the present invention.

In the above, 100 g of this skin-whitening liquid nutritional composition contained 100 mg of HW.

Example 7

Preparation of Skin-Whitening Drink 300 g of skim milk was dissolved in 409 g of deionized water, after which 1 g of HW obtained in Example 1 was dissolved and the mixture was heated to 50° C. and then agitated and mixed for 30 minutes using an ultra disperser (ULTRA-TURRAX T-25 by IKA Japan K.K.) operated at 9,500 rpm. The resulting mixture was mixed with 100 g of multitol, 2 g of acidifier, 20 g of reduced starch syrup, 2 g of fragrance and 166 g of deionized water, after which the mixture was filled in a 100-ml glass bottle and then sterilized at 90° C. for 15 minutes and tightly sealed, to prepare 10 skin-whitening drinks (each containing 100 ml) conforming to the present invention.

In the above, 100 ml of this skin-whitening drink contained 100 mg of HW.

Example 8

Preparation of Skin-Whitening Dog Food 200 g of HW obtained in Example 2 was dissolved in 99.8 kg of deionized water, after which the solution was heated to 50° C. and then agitated and mixed for 40 minutes using a homogenizing mixer (MARK II 160 by Tokushu Kika Kogyo Co., Ltd.) operated at 3,600 rpm, to obtain a HW solution containing 2 g/100 g of HW. Then, 10 kg of this HW solution was mixed with 12 kg of soybean meal, 14 kg of skim milk, 4 kg of soybean oil, 2 kg of corn oil, 23.2 kg of palm oil, 14 kg of corn starch, 9 kg of flour, 2 kg of bran, 5 kg of vitamin mixture, 2.8 kg of cellulose, and 2 kg of mineral mixture, after which the mixture was sterilized at 120° C. for 4 minutes to produce 100 kg of a skin-whitening dog food conforming to the present invention.

For your information, 100 g of this skin-whitening dog food contained 20 mg of HW.

What is claimed is:

1. A method for skin-whitening, comprising:
   providing a whey protein hydrolyzate having the following characteristics:
   (A) the molecular weight is distributed within 10 kDa with a main peak of 200 Da to 500 Da;
   (B) the APL (average peptide-chain length) is 2 to 8;
   (C) the free amino acid content is 20% or less; and
   (D) the antigenicity is one-ten thousandth of antigenicity of β-lactoglobulin or less; and
   orally administrating the whey protein hydrolyzate as a skin-whitening agent to a subject desiring skin-whitening, in an amount of at least 5 mg of the whey protein hydrolyzate per day,
   wherein the step of providing the whey protein hydrolyzate comprises:
   (i) enzymatically decomposing a whey protein as a preliminary decomposition using a protein hydrolyzing enzyme under pH 6 to 10 at 20 to 55° C., and then raising the temperature for further decomposition of the whey protein in step (ii); and
   (ii) enzymatically decomposing the hydrolyzed whey protein obtained in step (i) while thermally denaturing the hydrolyzed whey protein using a heat-resistant protein hydrolyzing enzyme under pH 6 to 10 at 50 to 70° C. until a main peak of the hydrolyzed whey protein is reduced to 200 Da to 500 Da as measured when concentrated using a molecular weight cut off in a range of 2 kDa to 10 kDa and in a range of 150 Da to 300 Da, and then heating the obtained product and thereby deactivating the enzyme.

2. The method according to claim 1, wherein the whey protein hydrolyzate is administrated to the subject at a concentration of 0.01 to 1%.

* * * * *